United States Patent
Harant et al.

(10) Patent No.: US 11,554,009 B2
(45) Date of Patent: Jan. 17, 2023

(54) INTRAOCULAR LENSES WITH INTRAOCULAR PRESSURE SENSORS AND METHODS OF MANUFACTURE

(71) Applicant: Qura, Inc., Framingham, MA (US)

(72) Inventors: Adam Harant, Oracle, AZ (US);
Douglas P. Adams, Sudbury, MA (US);
Amitava Gupta, Roanoke, VA (US)

(73) Assignee: Qura, Inc., Duxbury, MA (US)

( * ) Notice: Subject to any disclaimer, the term of this patent is extended or adjusted under 35 U.S.C. 154(b) by 0 days.

(21) Appl. No.: 17/612,110

(22) PCT Filed: May 17, 2019

(86) PCT No.: PCT/US2019/032912
§ 371 (c)(1),
(2) Date: Nov. 17, 2021

(87) PCT Pub. No.: WO2020/236139
PCT Pub. Date: Nov. 26, 2020

(65) Prior Publication Data
US 2022/0142768 A1    May 12, 2022

(51) Int. Cl.
*A61F 2/16* (2006.01)
*A61B 3/16* (2006.01)

(52) U.S. Cl.
CPC .............. *A61F 2/1627* (2013.01); *A61B 3/16* (2013.01); *A61F 2002/169* (2015.04); *A61F 2250/0002* (2013.01); *A61F 2250/0036* (2013.01)

(58) Field of Classification Search
CPC .............. A61F 2/1627; A61F 2002/169; A61F 2250/0002; A61F 2250/0036; A61B 3/16
See application file for complete search history.

(56) References Cited

U.S. PATENT DOCUMENTS

| | | | |
|---|---|---|---|
| 6,443,893 B1 * | 9/2002 | Schnakenberg | A61B 5/0031 600/398 |
| 6,796,942 B1 * | 9/2004 | Kreiner | A61B 5/0031 600/398 |
| 8,475,374 B2 | 7/2013 | Irazoqui et al. | |
| 8,834,566 B1 * | 9/2014 | Jones | A61F 2/1629 623/6.37 |
| 9,078,613 B2 | 7/2015 | Irazoqui et al. | |
| 9,173,564 B2 | 11/2015 | Choo et al. | |
| 9,596,988 B2 | 3/2017 | Irazoqui et al. | |
| 9,662,021 B2 | 5/2017 | Chow et al. | |
| 10,044,227 B2 | 8/2018 | Chappell et al. | |

(Continued)

FOREIGN PATENT DOCUMENTS

| | | |
|---|---|---|
| WO | 0219949 A2 | 3/2002 |
| WO | 2013090886 A1 | 6/2013 |

(Continued)

OTHER PUBLICATIONS

Biros et al., "Development of glaucoma after cataract surgery in dogs: 220 cases (1987-1998)." Journal of the American Veterinary Medical Association 216.11 (2000): 1780-1786.

(Continued)

*Primary Examiner* — Javier G Blanco
(74) *Attorney, Agent, or Firm* — Smith Baluch LLP (57) ABSTRACT

Intraocular lenses with pressure sensors embedded therein, and methods of manufacture.

19 Claims, 5 Drawing Sheets

(56) References Cited

U.S. PATENT DOCUMENTS

| | | |
|---|---|---|
| 10,426,341 B2 | 10/2019 | Choo et al. |
| 2001/0054774 A1 | 12/2001 | Altmann |
| 2005/0090612 A1* | 4/2005 | Soane ................. C08F 8/00 524/800 |
| 2005/0119740 A1* | 6/2005 | Esch .................. A61F 2/1635 623/6.37 |
| 2007/0135915 A1* | 6/2007 | Klima ................. A61F 2/1629 623/6.37 |
| 2009/0264998 A1* | 10/2009 | Mentak ............... A61F 2/1627 623/6.37 |
| 2010/0131059 A1* | 5/2010 | Callahan .............. A61F 2/1613 623/6.23 |
| 2010/0137694 A1 | 6/2010 | Irazoqui et al. |
| 2010/0234717 A1* | 9/2010 | Wismer ................ A61B 3/16 600/398 |
| 2013/0041245 A1* | 2/2013 | Cerboni .............. A61B 5/6821 600/398 |
| 2014/0058008 A1 | 2/2014 | Pinchuk et al. |
| 2016/0051143 A1 | 2/2016 | Rickard et al. |
| 2017/0164831 A1 | 6/2017 | Choo et al. |
| 2017/0209045 A1 | 7/2017 | Choo et al. |
| 2017/0293197 A1* | 10/2017 | Van Heugten ............ G02F 1/29 |
| 2018/0035888 A1 | 2/2018 | Irazoqui et al. |
| 2018/0375382 A1 | 12/2018 | Chappell et al. |
| 2019/0175015 A1 | 6/2019 | Adams et al. |
| 2020/0237218 A1 | 7/2020 | Irazoqui et al. |
| 2021/0030529 A1 | 2/2021 | Adams et al. |
| 2021/0052783 A1 | 2/2021 | Adams et al. |
| 2021/0137379 A1 | 5/2021 | Fehr et al. |
| 2021/0169427 A1 | 6/2021 | Adams et al. |

FOREIGN PATENT DOCUMENTS

| | | |
|---|---|---|
| WO | 2017210316 A1 | 12/2017 |
| WO | 2019191748 A1 | 10/2019 |
| WO | 2020023036 A1 | 1/2020 |
| WO | 2020046299 A1 | 3/2020 |
| WO | 2020081072 A1 | 4/2020 |
| WO | 2020160262 A1 | 8/2020 |
| WO | 2020236139 A1 | 11/2020 |

OTHER PUBLICATIONS

Cook, "Canine cataract surgery." Cataract & Refractive Surgery Today (2008): 32-34.

Gellat et al., "Prevalence of the breed-related glaucomas in pure-bred dogs in North America." Veterinary ophthalmology 7.2 (2004): 97-111.

International Search Report and Written Opinion in International Patent Application No. PCT/US2019/032912 dated Sep. 23, 2019, 16 pages.

* cited by examiner

INTRAOCULAR LENSES WITH INTRAOCULAR PRESSURE SENSORS AND METHODS OF MANUFACTURE

CROSS-REFERENCE TO RELATED APPLICATION(S)

This application is a national-stage application, under 35 U.S.C. 371, of International Application No. PCT/US2019/032912, which was filed on May 17, 2019, and is incorporated herein by reference. All publications and patent applications mentioned in this specification are herein incorporated by reference to the same extent as if each individual publication or patent application was specifically and individually indicated to be incorporated by reference.

BACKGROUND

Intraocular lenses (IOLs) are typically permanent, plastic lenses that are surgically implanted inside of the eyeball to replace or supplement the eye's natural crystalline lens. They have been used in the United States since the late 1960s to restore vision to cataract patients, and more recently are being used in several types of refractive eye surgery.

The natural crystalline lens is critical component of the complex optical system of the eye. The crystalline lens provides about 17 diopters of the total 60 diopters of the refractive power of a healthy human eye. Most intraocular lenses used in cataract surgery may be folded and inserted through the same tiny opening that was used to remove the natural crystalline lens. Once in the eye, the lens may unfold to its full size. The opening in the eye may be as small as 2.5 mm in length, so that it heals itself quickly without stitches. The intraocular lenses may be made of inert materials or they may have a biocompatible coating that does not trigger rejection responses by the body.

In most cases, IOLs are permanent. They rarely need replacement, except in the instances where the measurements of the eye prior to surgery have not accurately determined the required focusing power of the IOL In most cases, the intraocular lenses implanted during cataract surgery are monofocal lenses, and the optical power of the IOL is selected such that the power of the eye is set for distance vision. The patient still requires reading glasses after surgery. Intraocular lens implants may be multifocal lenses, which attempt to function more like the eye's natural lens by providing clear vision at a distance and reasonable focus for a range of near distances, for patients with presbyopia.

Recently, intraocular lenses have been implanted in canines, mainly household pet dogs, after cataract extraction. Commonly affected breeds include the American cocker spaniel, poodle, Boston terrier, miniature Schnauzer, Bichon Frise, and Labrador retriever. Typically, genetic lenticular opacities are bilateral and slowly progressive. Rapidly progressive cataracts commonly occur in dogs with diabetes mellitus. Secondary lens-induced uveitis is a frequent finding that may complicate pre- and postoperative management (Cook, C, "Canine Cataract Surgery", in *Cataract & Refractive Surgery Today*, 2008; pp 32).

Figure 1:
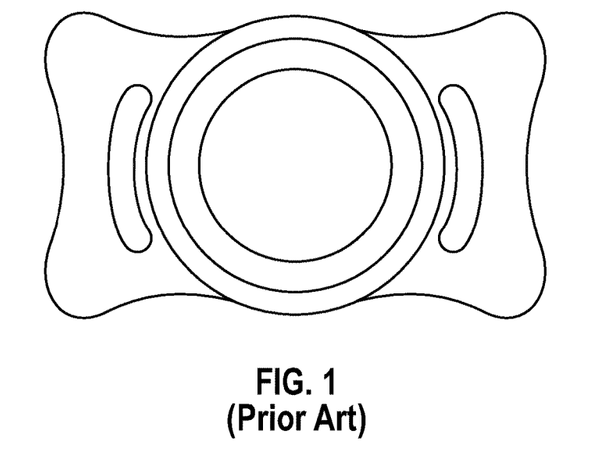
FIG. 1 shows an exemplary intraocular lens developed for implantation in canines.

An intraocular lens developed for implantation in canines is shown in FIG. 1, which may be a hydrophilic posterior chamber intraocular implant developed for canines.

Figure 2:
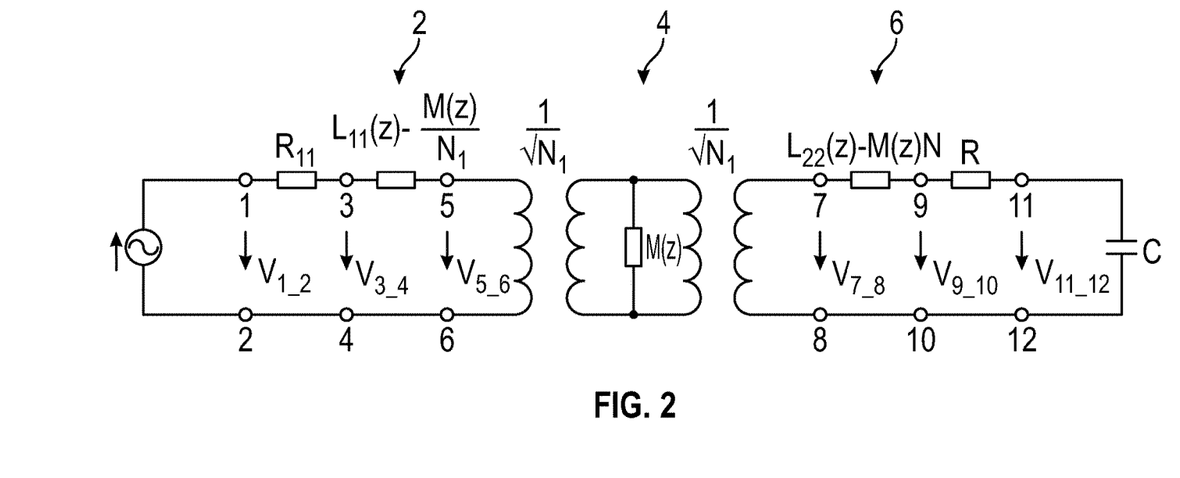
FIG. 2 shows an exemplary structural model of a telemetry link between an internal device and an external interrogating device.

A considerable number of patients needing to undergo cataract surgery have preexisting glaucoma. Glaucoma has been diagnosed in nearly 15% of the population in USA above age 80. The incidence of glaucoma rises with age, and is more prevalent in the African American and Hispanic population segment in USA, as shown in FIG. 2. Many of these patients develop cataract at an earlier age (typically between 50 and 75 years of age), and undergo cataract extraction and in virtually all cases implantation of an intraocular lens. Many of these pseudophakes or aphakes, especially those with diabetes may develop glaucoma, including angle closure glaucoma caused by post-operative inflammation.

Postoperative increase in intraocular pressure may be caused by residual viscoelastic gels left over after surgery, incursion of the vitreous caused by breach of the posterior capsule during cataract surgery, or iatrogenic damage to the iris, leading to pigment dispersion or the Ugh (uveitis-glaucoma-hyphema) syndrome. Moreover a certain percentage of persons who develop glaucoma at a relatively early age subsequently develop cataract and undergo cataract extraction and implantation of an intraocular lens.

Models based on UN world population projections predict that in the year 2020, 79.6 million persons will be afflicted with either open-angle glaucoma (OAG) or angle-closure glaucoma (ACG) with 5.9 million and 5.3 million projected to be bilaterally blind from these two conditions, respectively. (Kung, J S, et al, "Cataract surgery in glaucoma patient" in Middle east Afr J Ophthalmol, 2015; 22(1), pp 10-17.).

Occurrence of glaucoma after cataract surgery is especially prevalent in canines, partly because canines tend to experience a substantially higher level of postoperative inflammation subsequent to cataract surgery.

The prevalence of the primary breed-related glaucoma has gradually increased from 0.29% (1964-1973); 0.46% (1974-1983); 0.76% (1984-1993); to 0.89% (1994-2002). Breeds that consistently featured among the highest 10 for glaucoma prevalence from four different periods (1964 to 2002) included American Cocker Spaniel, Basset Hound, Wire Fox Terrier, and Boston Terrier. During the last observation period (1994-2002), 22 different breeds had 1% or higher prevalence of the glaucoma. The highest prevalence of glaucoma in 1994-2002 by breed included: American Cocker Spaniel (5.52%); Basset Hound (5.44%); Chow Chow (4.70%); Shar-Pei (4.40%); Boston Terrier (2.88%); Wire Fox Terrier (2.28%); Norwegian ElkHound (1.98%); Siberian Husky (1.88%); Cairn Terrier (1.82%); and Miniature Poodle (1.68%). A predominance of females with glaucoma occurred in the American Cocker Spaniel, Basset Hound, Cairn Terrier, Chow Chow, English Cocker Spaniel, Samoyed, and perhaps the Siberian Husky, and a predominance of males in the Australian Cattle dog and St Bernard. Age affected the time for first presentation of the glaucoma in the pure-bred dog. In the majority of breeds the glaucoma was presented for initial diagnosis in dogs between 4 and 10 years of age (Gellat K N, and McKay, E O, "Prevalence of the breed related glaucoma in pure bred dogs in North America", in *Vet Ophthalmol*, 2004; 7(21, pp 97).

Biros, et al, reported a study of 346 canine eyes, in which they monitored incidence of glaucoma as a function of eight variable, including breed, sex, post-operative hypertension, and intraocular lens placement. Of the 346 eyes, 58 (16.8%) developed glaucoma after surgery. At 6 months, 32 of 206 (15.5%) eyes examined had glaucoma; at 12 months, 44 of 153 (28.8%) eyes examined had glaucoma. Median follow-up time was 5.8 months (range, 0.1 to 48 months). Mixed-breed dogs were at a significantly lower risk for glaucoma, compared with other breeds. Eyes with IOL placement were at a significantly lower risk for glaucoma, compared with eyes without IOL placement. Eyes with hypermature cataracts were at a significantly higher risk for glaucoma, compared with eyes with mature or immature cataracts (Biros, et al, "Development of glaucoma after cataract surgery in dogs", in *J Am Vet Med Assoc.*, 2000; 216(11), pp 1780).

SUMMARY OF THE DISCLOSURE

One aspect of the disclosure is an intraocular lens ("IOL") adapted to sense intraocular pressure and adapted for implantation in an eye, comprising an optic portion disposed in a central region of the IOL; a haptic portion that extends radially outward relative to a periphery of the optic portion, the haptic portion comprising a substrate layer extending radially outward relative to the periphery of the optic portion, wherein the haptic portion also includes an intraocular pressure sensor secured to the substrate layer, the substrate layer also extending radially inward relative to the periphery of the optic portion and through the optic portion.

In some embodiments the optic comprises an anterior optic portion and a posterior optic portion spaced apart from the anterior optic portion by the substrate layer that extends through the optic portion, the anterior optic portion disposed anterior to the substrate layer in the optic portion, and the posterior optic portion disposed posterior to the substrate layer in the optic portion. The haptic portion may further comprises an electronics module disposed on the substrate layer, wherein the intraocular pressure sensor is disposed in the electronics module. The electronics module may further comprise at least one of a microcontroller or an ASIC. The electronics module may further comprise a rechargeable battery. The haptic portion may further comprise an antenna secured to the substrate layer.

In some embodiments the optic portion comprises first and second layers, wherein the substrate layer is disposed between the first and second layers in the optic portion.

In some embodiments the optic portion comprises anterior and posterior optic elements comprising a hydrophobic material.

In some embodiments the optic portion comprises anterior and posterior optic elements comprising a hydrophilic material.

In some embodiments the optic portion comprises an anterior optic layer with a first refractive index, and the substrate layer that extends through the optic portion having a second refractive index greater than the first refractive index. The optic portion may comprise a posterior optic layer, the substrate layer between the anterior optic layer and the posterior optic layer, wherein the posterior optic layer has a third refractive index that is the same as the first refractive index. The second refractive index may be from 1.45-1.80, such as from 1.5-1.75, such as 1.6-1.75, such as 1.65-1.75, such as from 1.68-1.72. The first refractive index may be from 1.42-1.56. An adhesive may bond the anterior optic layer to the substrate layer, wherein the adhesive has a refractive index that is between the first refractive index and the second refractive index. The adhesive refractive index may be a mean of the first refractive index and the second refractive index.

In some embodiments the substrate layer comprises at least one of a polyether, a polyamide, a polyimide, a polyester, or a cyclic olefinic copolymer.

In some embodiments the substrate layer extends radially around the entirety of the periphery of the optic portion.

In some embodiments the substrate layer has a tensile modulus in the range of 2-10 GPa measured at 25 C.

In some embodiments the substrate layer has a melting point in excess of 100 C.

In some embodiments the substrate layer has a glass transition temperature in excess of 75 C.

In some embodiments the substrate layer has a thickness from 5-25 microns. A thickness of the optic portion may be from 100-400 microns.

In some embodiments the substrate layer comprises at least two layers, at least one of which comprises a cross-linked thermoset and at least one of which comprises a partially crystalline thermoplastic material.

One aspect of the disclosure is an IOL adapted to sense intraocular pressure and adapted for implantation in an eye, comprising: an optic portion disposed in a central region of the IOL; a haptic portion that extends radially outward relative to a periphery of the optic portion, the haptic portion comprising a haptic substrate layer extending radially outward relative to the periphery of the optic portion, wherein the haptic substrate layer has a thickness from 5-25 microns, and wherein the haptic portion also includes an intraocular pressure sensor secured to the substrate layer.

The IOL may further comprise any of the features herein.

One aspect of the disclosure is an IOL adapted to sense intraocular pressure and adapted for implantation in an eye, comprising: an optic portion disposed in a central region of the IOL; a haptic portion that extends radially outward relative to a periphery of the optic portion, the haptic portion comprising a substrate layer extending radially outward relative to the periphery of the optic portion, wherein the haptic substrate layer has a tensile modulus in the range of 2-10 GPa measured at 25 C, and wherein the haptic portion also includes an intraocular pressure sensor secured to the haptic substrate layer.

The IOL may further comprise any of the features herein.

One aspect of the disclosure is a method of manufacturing an IOL, comprising: bonding an anterior optical component to a first side of a haptic substrate layer; and bonding a posterior optical component to a second side of the haptic substrate layer, such that the haptic substrate layer is disposed between the anterior optical component and the posterior optical component.

The haptic substrate layer may have an outermost dimension greater than an outermost dimension of the anterior optical component and an outermost dimension of the posterior optical component.

The haptic substrate layer may have a higher refractive index than a refractive index of the anterior optical component and a refractive index of the posterior optical component. The bonding steps may comprise bonding the optical components to the haptic substrate layer with an adhesive that has a refractive index between the refractive index of the haptic substrate layer and the optical components.

The method may further comprise, at a time subsequent to the bonding steps (but not necessarily immediate thereafter), reshaping surfaces of the anterior optical component and the posterior optical component.

The method may further comprise, at a time subsequent to the bonding steps (but not necessarily immediate thereafter), reshaping an outer profile of the haptic substrate layer to form haptics.

The method may further comprise, at a time subsequent to the bonding steps (but not necessarily immediate thereafter), depositing at least one of the following on the haptic substrate layer: an electronics module or an antenna.

The method may further comprise any suitable feature herein.

One aspect of the disclosure is a method of manufacturing an IOL, comprising: providing a haptic substrate layer; removing a central optic region of the haptic substrate layer; depositing at least of an electronics module or an antenna on the haptic substrate layer with the central region removed therefrom; machining an optic body; and bonding the optic body in the central optic region of the haptic substrate layer.

The method may further comprise any suitable feature herein, including in any IOL or method.

DETAILED DESCRIPTION

The present disclosure relates to field of Intraocular Lenses ("IOLs") that include a sensor, including manufacturing processes thereof. In some embodiments a sensor is coupled to a haptic surface of the IOL, ensuring that the sensor is not within the optic zone such that it does not significantly affect the optical performance or stability of the IOL in the eye. Preferably, the sensor is an intraocular pressure sensor.

Regular and frequent monitoring of intraocular pressure is critically important during the immediate post-operative period, following cataract surgery. In the long run, regular monitoring of intraocular pressure is required to track continued efficacy of pressure controlling medications and monitor compliance. Both of these needs require introduction of an implanted, intraocular pressure sensor that can wirelessly transmit data to an external unit without any involvement of the patient.

Preferably, the IOP sensor assembly is mounted on the body of the IOL. The sensor assembly (which may be referred to herein as an implantable wireless intraocular pressure sensor assembly or WIPSA) can comprise the sensor, an electronic controller, a memory to store IOP data and telemetry algorithms that may be customized for each patient or animal implanted with a IOP sensor, an antenna and a radiofrequency (RF) module that performs telemetry transmitting data on intraocular pressure generated by the intraocular pressure sensor to an external monitoring unit (which may be referred to herein as an external interrogating device, or EID). Exemplary implantable devices and external units, including their design, are described in WO 2017/210316, which is incorporated by reference herein.

An exemplary structural model of a telemetry link 4 between an internal device 6 and an external interrogating device 2 is shown in FIG. 2. The structural model of the telemetry link shown in FIG. 2 is shown for a passive implant 6 with no indigenous power source. The parameters and their ranges are shown in Table 2. The telemetry link shown can be used for any of the IOL's herein, which can be considered the internal device.

The maximum operating range of such a telemetry link is shown in Table 2.

In some uses, the implants are implanted in canines and are used to monitor canine IOP. In such instances, the EID is preferably adapted such that it can be attached to the collar worn by the dog, or it is clipped on to its vest or other similar clothing. In such a configuration, the EID may be programmed to automatically activate the implanted sensor assembly initiating data collection and transmission without requiring intervention by the owner of the canine. A study was performed to measure the average distance of the EID from the WIPSA for a number of common dog breeds that are found among household pets. The data are presented in Table 1. Comparison of these data with the range of operating parameters of a passive telemetry link shown in Table 2 indicate that the minimum distance over which wireless data transfer has to be carried out is about 15 cm, and should be in a range of 15.0+/−3.0 cm. This requirement makes it necessary to have an indigenous power source in the sensor assembly, in order to maintain the RF power in the EID at a safe level, and remain in compliance with regulatory requirements in all operating situations. Consequently, the implantable device preferably includes a rechargeable power source (e.g., battery) or some other power source that is controlled by a power management module, and that is recharged wirelessly by the same external unit using the same wireless data transfer module. The external unit has a wireless data exchange and power transfer module powered by a rechargeable battery that can be recharged on a regular basis by any electrical power outlet.

TABLE 1

Distance of a dog collar from the eye in selected canine breeds.

| # | breed | weight (kg) | distance collar - eye (inch) | distance collar - eye (cm) | std-dev (cm) |
| --- | --- | --- | --- | --- | --- |
| Small | average | <15 kg | 4.3 | 10.9 | 3.0 |
| | maltese | 5 | 3.5 | 8.9 | |
| | shih tsu | 8 | 3.5 | 8.9 | |
| | dachshund | 9 | 4.5 | 11.4 | |
| | bichon frise | 10 | 5 | 12.7 | |
| | border terrier | 10 | 4 | 10.2 | |
| | japanese chin | 10 | 3 | 7.6 | |
| | cocker spaniel | 13 | 6.5 | 16.5 | |
| Medium | average | 15-22 kg | 4.7 | 11.9 | 3.9 |

TABLE 1-continued

Distance of a dog collar from the eye in selected canine breeds.

| # | breed | weight (kg) | distance collar - eye (inch) | distance collar - eye (cm) | std-dev (cm) |
|---|---|---|---|---|---|
| | beagle | 15 | 5 | 12.7 | |
| | miniature poodle | 15 | 3 | 7.6 | |
| | blue heeler | 22 | 6 | 15.2 | |
| Large | average | >22 kg | 5.7 | 14.5 | 4.4 |
| | taz | 25 | 4 | 10.2 | |
| | golden retriver | 30 | 6.5 | 16.5 | |
| | matie | 30 | 6 | 15.2 | |
| | labrador | 31 | 8 | 20.3 | |
| | corgi | 33 | 4 | 10.2 | 3.8 |
| Total | average | — | 4.8 | 12.3 | |

TABLE 2

Parameters of the telemetry link in FIG. 2 and their values.

| Symbol | Parameter Description | Value | Unit |
|---|---|---|---|
| $d_{Cu1}$ | Reader coil wire diameter | 0.50 | mm |
| $ID_1$ | Inner diameter of reader coil | 30.0 | mm |
| $n_1$ | Number of turn of the reader coil | 2 | 1 |
| $L_{11}$ | Self-inductance of the reader coil | 256.2 | nH |
| $R_{11}$ | Reader coil wire resistance at operating frequency | 191 | mΩ |
| $d_{Au2}$ | Sensor coil wire diameter | 40 | μm |
| $ID_2$ | Inner diameter of sensor coil | 6.0 | mm |
| $n_2$ | Number of turns of the sensor coil | 16 | 1 |
| $L_{22}$ | Self-inductance of the sensor coil | 3.384 | μH |
| $R_{22}$ | Sensor coil wire resistance at operating frequency | 6.615 | Ω |
| $C_{sens}$ | Typical sensor capacitor value | 6.0 | pF |
| $f_0$ | Telemery link reference frequency | 35.323 | MHz |
| $z_{min}$ | Minimum coupling distance | 10 | mm |
| $z_{max}$ | Maximum coupling distance | 40 | mm |

Figure 3:
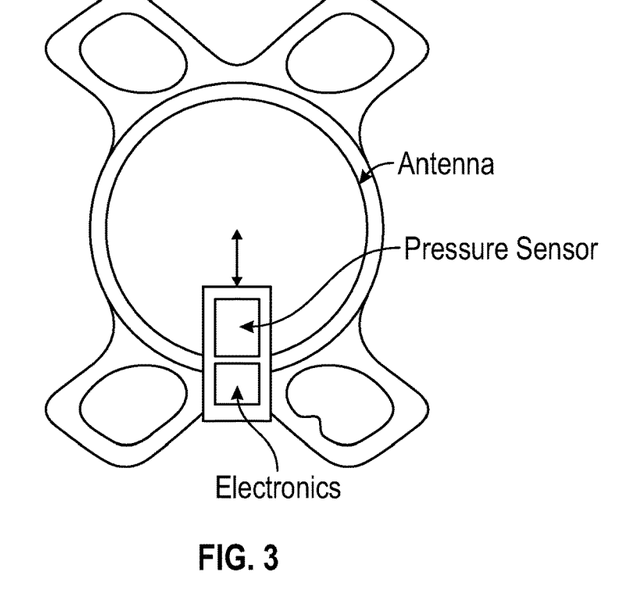
FIG. 3 illustrates an exemplary IOL with a sensor assembly disposed into or onto the optic portion of the IOL, with the antenna positioned around the periphery of the optic.

When considering designs for an intraocular lens comprising a pressure sensor, there are a variety of design pathways for integration of a sensor assembly into an IOL. An exemplary first design is to dispose the sensor assembly into or onto the optic portion, and the antenna positioned around the periphery of the optic, as shown in exemplary FIGS. 3 and 4. Exemplary folding or bending lines are illustrated in the design in FIG. 4. Exemplary locations of exemplary components are shown in FIG. 3. Additional exemplary details of such IOLs can be found in PCT App. No. PCT/US2019/025102, filed Apr. 1, 2019, the entire disclosure of which is fully incorporated by reference herein for all purposes.

Figure 4:
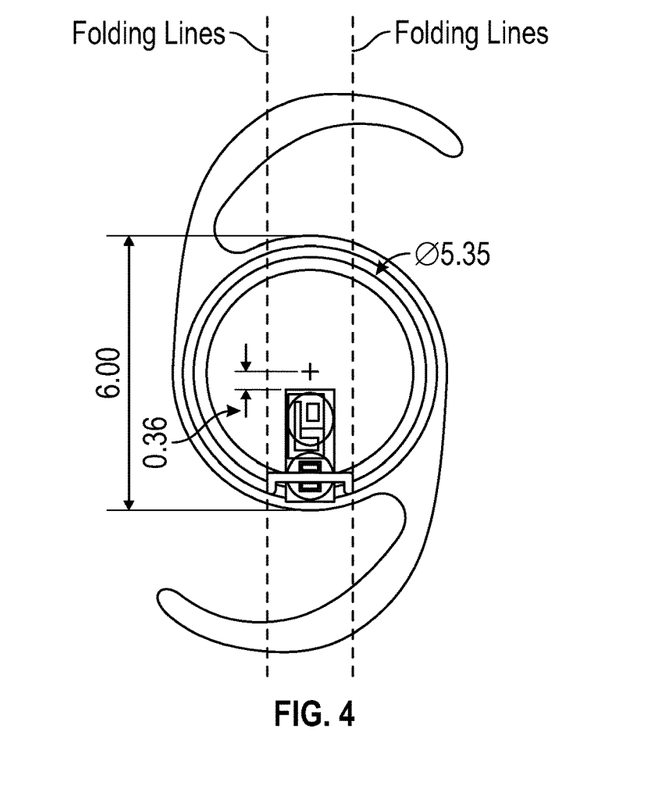
FIG. 4 illustrates an exemplary IOL with a sensor assembly disposed into or onto the optic portion of the IOL, with the antenna positioned around the periphery of the optic.

In the embodiment in FIG. 3, the diameter of the loop antenna can be in the range of 5.0 mm-7.0 mm, such as in the range of 5.5 mm to 6.5 mm. The antenna can be made of a wire of diameter 100 microns (range 25-200 microns), and can be mounted on the anterior surface of the intraocular lens. The antenna can be seated on a seat shaped in the form of a circular crevice built into a coating on the intraocular lens. The IOL design shown in FIG. 4 is based on an IOL designed for a two point fixation in the capsular bag, utilizing a modified C-loop design. The designs in both FIG. 3 and FIG. 4 share a common downside, which is that a portion of the sensor module or other electronics are at least partially disposed within the optical zone, thus compromising vision through the intraocular lens optic portion.

Figures 5A, 5B, 5C:
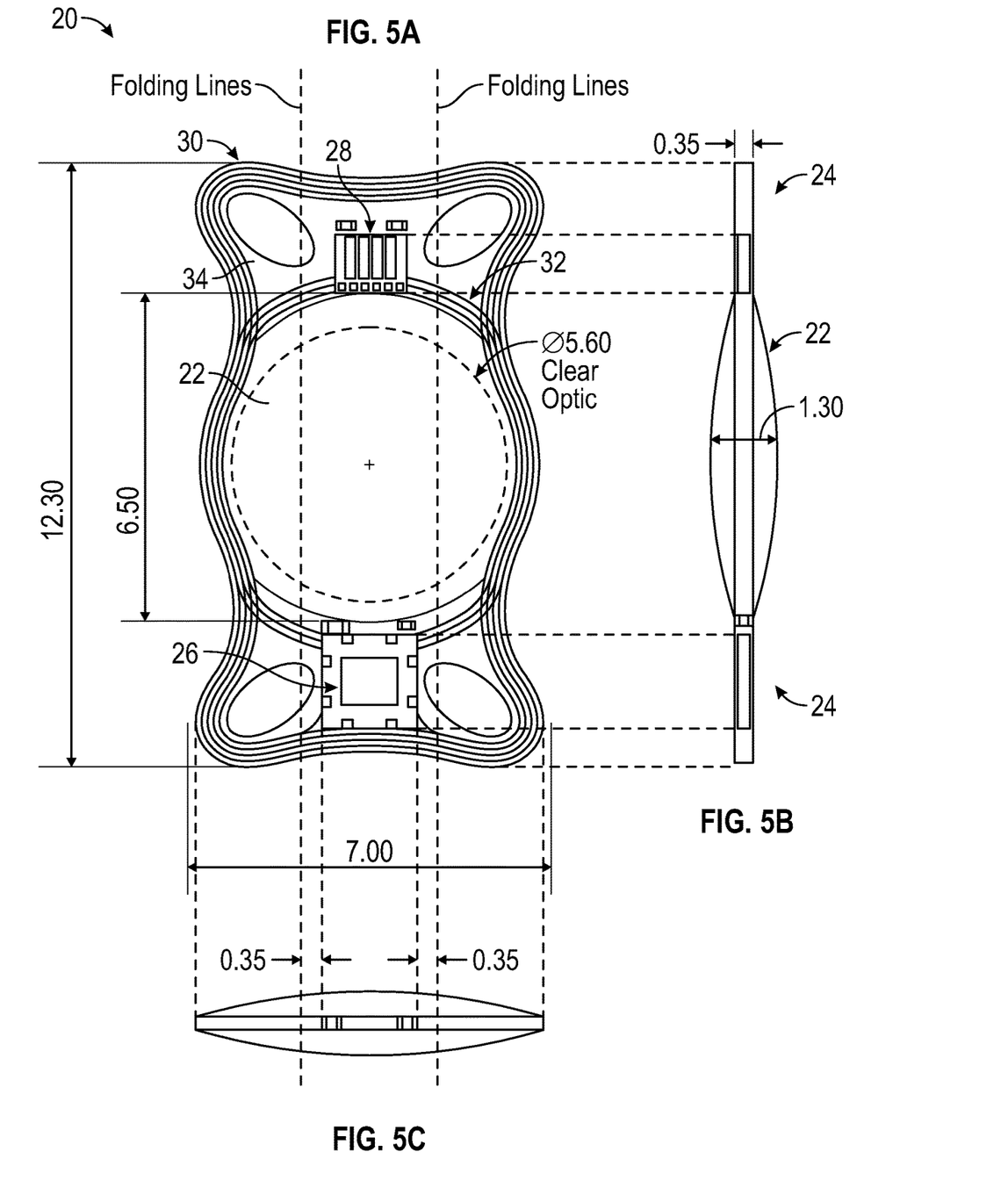
FIGS. 5A, 5B and 5C illustrates an exemplary IOL in which an optic portion of the IOL is free or substantially free of electronics.

An alternative design that addresses the downside of having electrical components disposed in the optic path (e.g., like in FIGS. 3 and 4) is to position the sensor assembly in or on the haptic and/or the haptic optic junction, and to position the antenna around the periphery of the haptic, as shown in exemplary FIG. 5A-C. Additional exemplary details of such IOLs can be found in PCT App. No. PCT/US2018/056277, filed Oct. 17, 2018, the entire disclosure of which is fully incorporated by reference herein for all purposes.

Referring to the embodiment shown in FIGS. 5A, 5B and 5C, a foldable multilayer intraocular lens 20 comprises an optic body 22 that may be made of a transparent hydrophobic or a hydrophilic material. IOL 20 includes haptic portion 24, to which sensor module 26 and electronics module 28 are coupled, which are in electrical communication via electrical connectors 32. The IOL also includes antenna 30, which extends around the periphery of the IOL, including the haptic, as shown, and is in electrical communication with connectors 32. Exemplary dimensions between the folding lines and sensor module 26 are 0.1 mm to 0.6 mm, such as 0.2 mm to 0.45 mm, such as 0.35 mm. Other dimensions shown in FIG. 5A are illustrative and not necessarily limiting. As can be seen in the side views of FIGS. 5B and 5C, sensor module 26 and electronics module 28 are secured to a haptic surface of the haptic portion. The electronics (e.g., 26 and 28) and the antenna 50 are preferably deposited on a flexible, transparent film substrate layer 34, functioning as a transparent printed circuit board ("PCB") and also as a haptic layer of the multilayer intraocular lens. This substrate film layer is preferably a thermoset or a partially crystalline polymer that is resistant to relatively high temperatures that may be required for electrical assembly, such as wire bonding or flip chip assembly or chemical vapor deposition processes. Assembly temperatures of 100 C or above may be required.

The multilayer intraocular lens 20 is comprised of two or more layers throughout, at least one of these layers comprising a relatively soft, cross-linked optic material, which may be an acrylic thermoset or a cross-linked polysiloxane. Another layer comprises a relatively stiff material that is selected on the basis of its ability to function as a substrate for electronics and the antenna assembly, as described above.

Two issues related to the design of a multilayer intraocular lens need to be addressed in order to obtain an implant that provides excellent optical resolution and mechanical characteristics, in particular bending, flexing behavior, as well as shape memory and fatigue resistance required of a foldable intraocular implant that will be expected to function for more than 20 years. The first of these design issues relates to the mismatch in refractive index between the materials comprising the haptics and the optics layers. The second issue is related to the high modulus and hence stiffness of the material comprising the haptic layer relative to the material comprising the optics layer.

Refractive index ("RI") of foldable acrylic or silicones commonly utilized in intraocular optic fabrication range from 1.42-1.44 for silicones, 1.44-1.49 for hydrophilic acrylics and from 1.44-1.56 for hydrophobic acrylics. In any of the embodiments herein, the RI of one or more optical components can therefore be from 1.42-1.56.

The haptic layers herein that are adapted to function as transparent PCB substrates typically have a relatively high refractive index, such as in the range from 1.45-1.80, measured at 535 nm.

Figure 6:
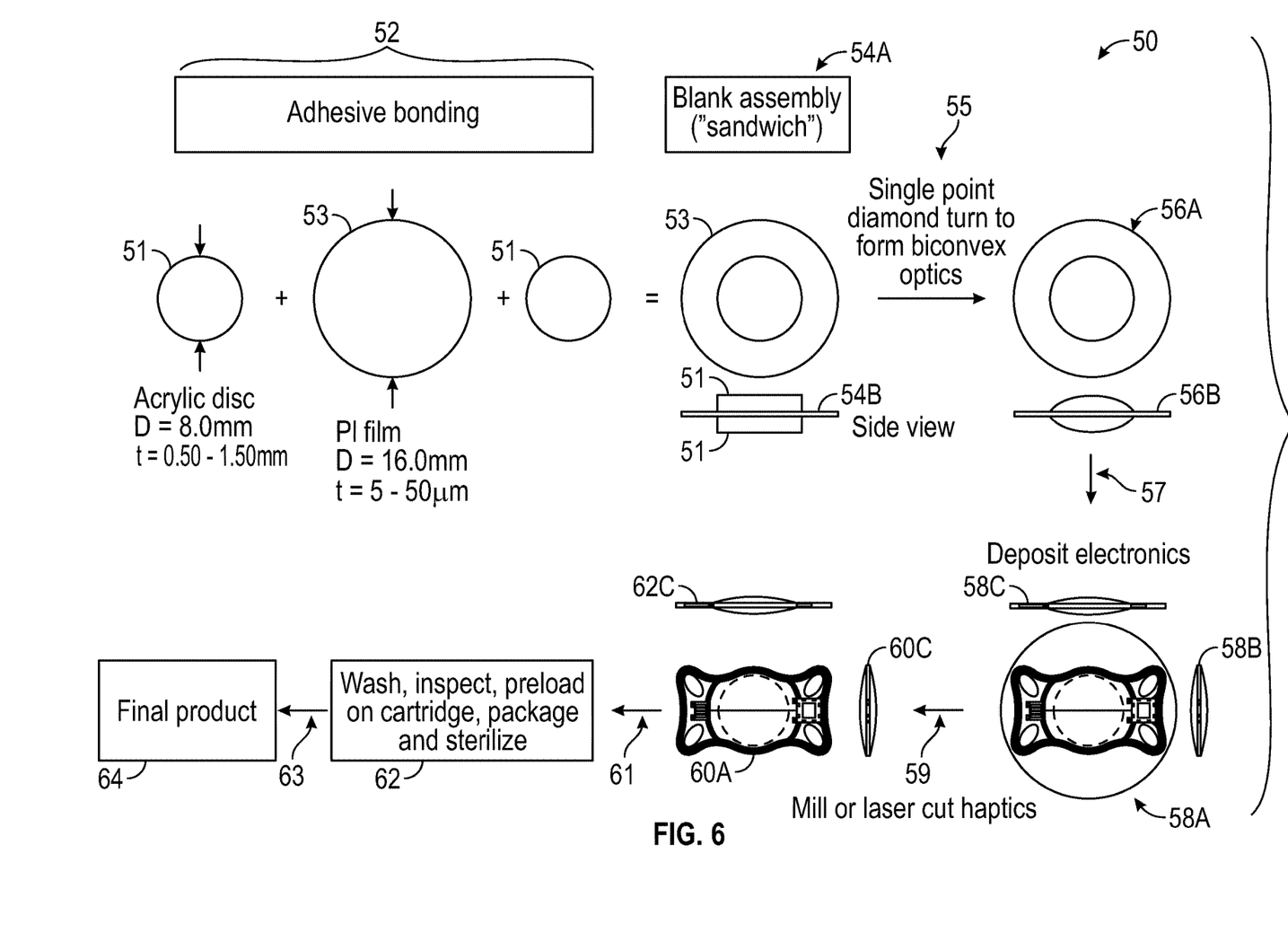
FIG. 6 illustrates an exemplary method of manufacturing an IOL with a pressure sensor.

FIG. 6 illustrates an exemplary process of manufacturing an IOL, the final product of which may have all or substantially the same components as the IOL in FIG. 5. In step 52, an initial bonding step occurs between three different components. First and second optic components are bonded to haptic substrate layer 53, one on each side of film layer 53. Exemplary diameters ("D") and thicknesses ("t") are provided. Optical components 51 can be discs (or buttons) and may be, by way of example, acrylic. Haptic layer 53 may be, for example without limitation, a polyimide material. FIGS. 5A and 54B show top and side views, respectively, of the sandwiched assembly of optical components 52 and haptic layer 53. This is considered the blank assembly sandwich.

Bonding the optic materials 51 (e.g., acrylic) to the haptic material 53 can be accomplished by acrylic adhesives, silicone adhesives, or hot melt adhesives, for example. Either a one part or two-part adhesive may be used. A two-part adhesive may be thermally polymerizable or it may be photopolymerizable.

After the blank has been prepared by bonding two acrylic buttons to the haptic film substrate as shown in views 54A and 54B, the assembly can be mounted on a block and diamond turned to form the biconvex optic based on computation of the optimum radii of curvature and base thickness of the acrylic layers, as described herein. Optics of any power may be machined, although for canine applications, a single power, 41D is preferred. Well known IOL power calculation algorithms can be used to calculate the power of the IOL needed.

In some embodiments, the optic components comprises a hydrophilic material. The hydrophilic material is preferably a cross-linked network of hydrophilic monomers, with an equilibrium water content of 5% to 50%, preferably 10% to 30%, more preferably 15-20%. In these embodiments, bonding of the hydrophilic optic component(s) and the haptic layer is preferably accomplished by developing an interpenetrating network anchored on both surface through siloxane, ester or amide linkages, as an example only, using silane coupling reaction or click chemistry.

After the optics have been machined, as shown in views 56A and 56B, the part is cleaned, and is then ready for deposition of the electronics, which occurs at step 57. The optic area is preferably masked during electronic deposition in order to avoid damage to the optics. A mask made of a metal or silicon or a poly-silicate film may be used to protect the acrylic optics during the deposition and assembly of the electronics.

Placement of the sensor assembly can include deposition of the antenna using a chemical vapor deposition process, a flip chip assembly followed by wire bonding of the microcontroller, the IOP sensor, the battery and the electronics that are mounted directly on the haptics substrate, as shown in the top and side views of parts 58A, 58B, and 58C. The profile of the haptic layer 53 is shown in FIG. 58A relative to the final cut shape of the haptic layer is shown. In step 59, the haptics are cut to the final outer profile, as shown in the views of parts 60A, 60B, and 60C. This process may be accomplished by, for example, laser cutting, die cutting or by using a CNC milling machine, utilizing a diamond tipped end mill.

The IOL thus formed is next coated by chemical vapor deposition with a multilayer hermetically sealing coating, for example, comprising or consisting of alternate layers of SiOx and Paralyene C. Each layer of such a coating may be, in some embodiments, 0.5-1.5 microns in thickness. Up to 16 layers may be applied, with the outermost layer being either Paralyene C or SiOx, depending on whether a hydrophilic or a hydrophobic optic surface is desired. The hermetic seal is not applied on the surface of a hydrophilic optic material (if the optic is made from a hydrophilic material), but is still necessary to provide added biocompatibility to the haptic layer. Any hydrophilic optic material herein would not receive a hermetic sealing thereon.

The IOL can then be coated with a hydrogel coating, comprising one or more layers of a biocompatible hydrogel, of thickness in the range of, for example, 25-50 microns. The coating may comprise, for example, polyethylene glycol mono-acrylate or polyethylene glycol diacrylate. The biocoating is applied by dipping or spraying the IOL with a monomer formulation comprising a photo-initiator such as Ethyl (2,4,6-trimethylbenzoyl) phenyl phosphinate (TPO-L). If such a coating is applied to the IOL, the coating is required to be dehydrated prior to sterilization by exposure to ETO or another chemical gas sterilant. Preferably, dehydration is carried out by maintaining the lens in a vacuum oven at 45 C (40-50 C) overnight. The IOL is then inspected, packaged and sterilized prior to shipment at step 62 and 64.

The optic components herein (such as components 51) may be made of a hydrophilic optic material. Referring again to FIG. 6, for example, buttons 51 can comprise a hydrophilic acrylate material that has been dehydrated prior to processing. Typically, the equilibrium water uptake of a hydrophilic material is in the range 2%-25%, more preferably 2-10%. Equilibrium water uptake should be maintained below 10% in order to minimize shear stress at the optic portion-haptic interface. The exemplary blank formation process, formation of the optics, the deposition and assembly of the antenna and the sensor assembly (such as those in FIG. 6) can be identical for both hydrophobic and hydrophilic optic materials. However, it is inappropriate to apply a multilayer hermetic sealing coating on a hydrophilic optic component. For processes herein that use hydrophilic optics, the mask applied on the optic before depositing the antenna and sensor electronics is therefore left in place when applying the multilayer hermetically sealing coating. Subsequently, the mask is removed prior to applying the biocompatible hydrogel coating. The IOL is then placed in deionized water, and sterilized by exposure to gamma radiation.

As set forth above, the haptic, or substrate, layer (e.g., layer 53 in FIG. 6) can have a refractive index higher than the anterior and posterior optic components 51. In the embodiment in FIG. 6 in which the haptic layer extends into and through the optic portion, this type of three-layer construction of the optic will lead to reflections of light at the two interfaces of the haptic and optic layers, causing an increase in light scatter, and lower image contrast. These interface reflections can be minimized by using an adhesive that is of a refractive index that is somewhere in between the refractive indexes of the haptic substrate layer and the optic component. In some embodiments, an adhesive can have a refractive index that is the geometric mean of the refractive indices of the optic layer and the haptic substrate layer, measured at the same wavelength. For example, bonding an optic layer of refractive index 1.50 to a haptic substrate layer that is a polyimide layer of refractive index 1.70 will create a refractive index mismatch of 0.2 units, leading to a loss of 6% or more of incident light due to interfacial light scatter. Using an adhesive of refractive index 1.59 (geometric mean of 1.50 and 1.70) will substantially reduce this interface light scatter, to less than 2%. Choosing adhesive properties is thus one manner in which the interface reflections can be reduced.

A second consideration related to the mechanical design of the multilayered IOL is the stiffness of the haptic layer (e.g., layer 53). The haptic layer material that support the electronics and the antenna are generally stiff, having a relatively high melting point in excess of 100 C, a glass transition temperature in excess of 75 C, and a tensile modulus in the range of 2-10 GPa measured at 25 C. This layer is bonded to the optic components (e.g., components 51), which are relatively soft, which may have glass transition temperatures in the range of 0-20C, and tensile moduli in the range 0.5-100 MPa.

The overall haptic portion thickness, including any electronics or sensor housings secured to the haptic layer, will generally be in the range from 0.125 mm-0.500 mm, depending on the tensile moduli of the materials comprising the haptic and the optic layers.

The thickness of the relatively rigid haptic substrate (which may be herein referred to as the haptic layer) is generally from 5 microns-25 microns, while the thicknesses of the relatively more flexible optical component (which may be referred to herein as the optic layer) is in the range of 0.100 mm-0.400 mm. Standard IOLs may have haptic thicknesses in the range of 0.4 mm to 0.5 mm.

In some embodiments, such as that shown in FIG. 6, the completed optic comprises three layers including an upper (or anterior) layer of an acrylic polymer, an intermediate layer of a haptic substrate layer and a bottom (or posterior) layer of an acrylic material that may be the same as the uppermost layer. Preferably, the optic is designed using an eye model such as the Leu Brennan eye model, or a wide-angle eye model such as that developed by Artal, and an IOL design that comprises the three layer geometry. A merit function is formulated computing and minimizing the difference between the target power and actual power of the IOL as a function of the curvatures of the acrylic surfaces and the base thickness of the acrylic layer in order to obtain the optimum values of the input parameters.

Any of the optical components herein may comprise a hydrophobic material. The hydrophobic acrylic material may be a cross-linked thermoset including acrylate and methacrylate derivatives (e.g., mono or multifunctional monomers with an acrylate or a methacrylate moiety as terminal or pendant groups), may have a refractive index in the range of 1.44-1.52 at 530 nm, and may have a glass transition temperature in the range 0 C to 25 C. It may be polymerized using thermal or photochemical initiators.

Any of the substrate layers herein utilized for deposition of sensor assembly, antenna and formation of haptics may be a thermoset or a thermoplastic material of relatively high melting temperature in the range 100-250 C, glass transition temperature exceeding 45 C, a tensile modulus not to exceed 5 GPa, and an elongation at break exceeding 25%. It should be transparent, and preferably colorless. It may comprise a polyester, a polyether, a polysulfone, a polyamide, a polyimide or cyclic olefinic polymers or copolymers, or Paralyene. It may be a single or a multilayer film.

The IOL created by the exemplary process in FIG. 6 is an example of an intraocular lens ("IOL") adapted to sense intraocular pressure and adapted for implantation in an eye, comprising an optic portion disposed in a central region of the IOL, a haptic portion that extends radially outward relative to a periphery of the optic portion, the haptic portion comprising a substrate layer extending radially outward relative to the periphery of the optic portion, wherein the haptic portion also includes an intraocular pressure sensor secured to the substrate layer, and the substrate layer also extending radially inward relative to the periphery of the optic portion and through the optic portion.

In the embodiment in FIG. 6, the optic comprises an anterior optic portion and a posterior optic portion spaced apart from the anterior optic portion by the substrate layer that extends through the optic portion, the anterior optic portion being disposed anterior to the substrate layer in the optic portion, and the posterior optic portion disposed posterior to the substrate layer in the optic portion. The haptic portion further comprises an electronics module secured to the substrate layer, wherein the intraocular pressure sensor is disposed in the electronics module. The electronics module may further comprise at least one of a microcontroller or an ASIC. The electronics module may further comprise a rechargeable battery. The haptic portion may further comprise an antenna secured to the substrate layer.

In the embodiment in FIG. 6 the optic portion comprises an anterior optic layer with a first refractive index, and the substrate layer that extends through the optic portion has a second refractive index greater than the first refractive index. The optic portion also comprises a posterior optic layer, the substrate layer between the anterior optic layer and the posterior optic layer, wherein the posterior optic layer has a third refractive index that is the same as the first refractive index. In the embodiment in FIG. 6, the second refractive index can be from 1.45-1.80, such as from 1.5-1.75, such as 1.6-1.75, such as 1.65-1.75, such as from 1.68-1.72. The first refractive index can be from 1.42-1.56.

In the embodiment in FIG. 6, an adhesive bonds the anterior and posterior optic layers to the substrate layer, wherein the adhesive has a refractive index that is between the first refractive index and the second refractive index. The adhesive refractive index can be a mean of the first refractive index and the second refractive index.

In the embodiment in FIG. 6, the substrate layer can comprise at least one of a polyether, a polyamide, a polyimide, a polyester, or a cyclic olefinic copolymer.

In the embodiment of FIG. 6, the substrate layer extends radially around the entirety of the periphery of the optic portion.

In any of the embodiments herein the substrate layer can have a tensile modulus in the range of 2-10 GPa measured at 25 C.

FIG. 6 is an example of an IOL with a substrate layer that has a thickness from 5-25 microns, and optionally wherein a thickness of the optic portion is from 100-400 microns.

Figure 7:
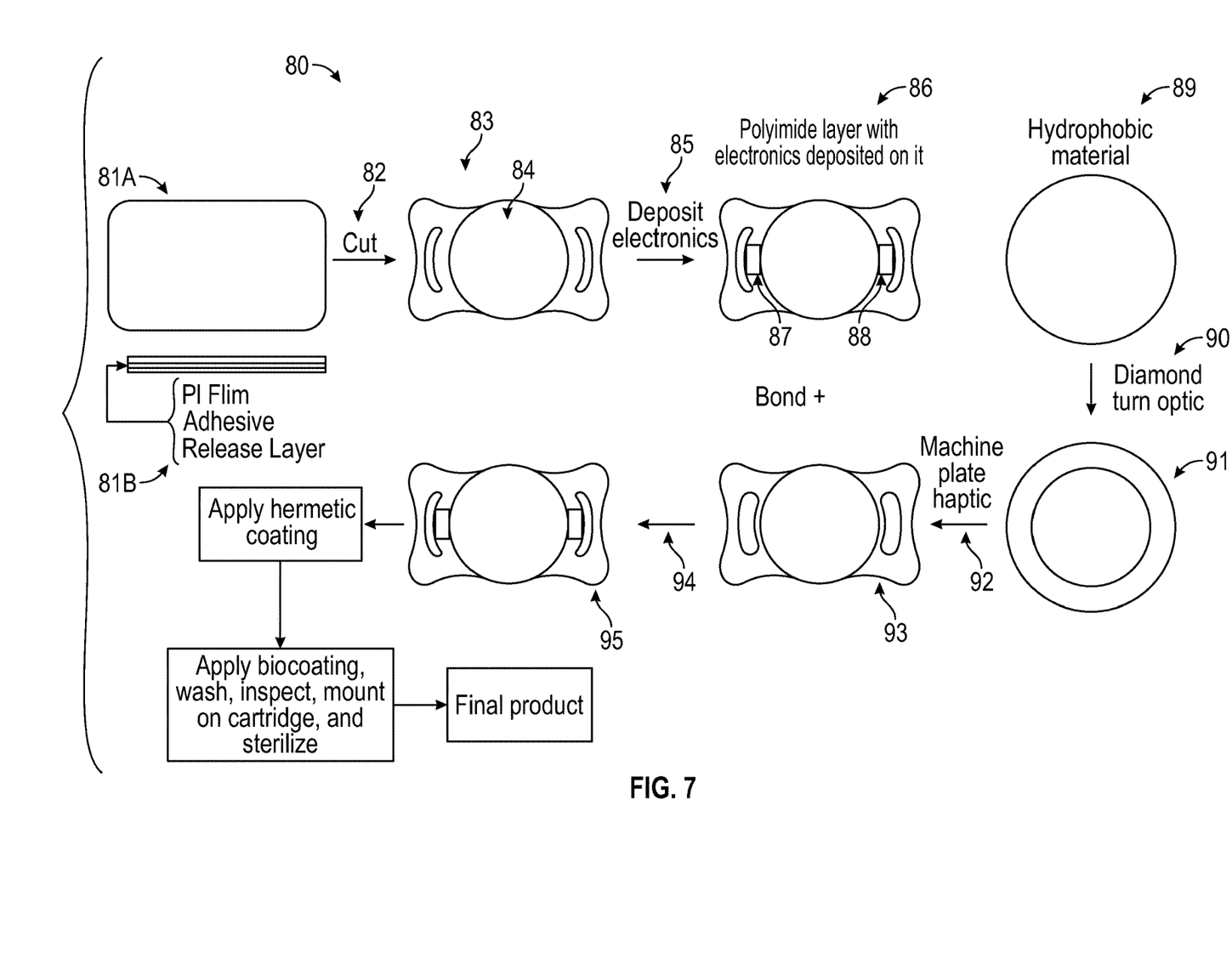
FIG. 7 illustrates an exemplary method of manufacturing an IOL with a pressure sensor.

FIG. 7 illustrates an exemplary method that can be used to create any of the IOLs herein. One difference between the finished IOL in the processes of FIGS. 6 and 7 is that an IOL resulting from the process in FIG. 7 does not have a substrate layer that extends in the haptic portion of the IOL and also extends all the way through the optic portion of the IOL. In the embodiment specifically shown in FIG. 7, the haptic layer does not extend into the optic portion of the IOL.

In the exemplary method 80 shown in FIG. 7, a starting layer is shown in top view 81A and side view 81B, which is a substrate layer in this embodiment. As shown in the side view 81B, the substrate layer includes top film layer, an adhesive, and a release layer on the bottom. The substrate layer can be any of the substrate layer materials herein, such as a polyimide layer. The haptic layer is then cut at step 82 to shape to form the haptic 83 leaving a circular opening 84 to accommodate an optic portion. At step 85 the electronic(s) and antenna are deposited on the haptic layer. At step 89 an optic button or other starting material 89 is provided. The optic material 89 is machined with the desired anterior and posterior curvatures, optionally from an acrylic or silicone material, and bonded to the haptic layer using an adhesive. The adhesive layer is typically 1-5 microns in thickness. The assembly with optic bonded thereto is then coated with a multilayer, hermetic coating as shown prior to further processing, provided that the optic comprises a hydrophobic material.

If a hydrophilic optic material is used, then the haptic layer with the assembled electronics is first coated with a hermetically sealing multilayer coating, prior to bonding the optic layer to the haptic layer.

The resulting multilayer intraocular lens according to the method of FIG. 7 may have superior optics, since it does not have optical interfaces as does an IOL made according to the method in FIG. 6.

In the embodiments herein, the optic portion is free of electronics and an antenna that may interfere with light passing through the optical path. It may be acceptable for one or more of electronics or an antenna to extend to a very small degree on the optic portion without substantially interfering with light passage through the optic path. If the disclosure herein thus states that the optical path is void of electronics and antenna, it may include a very minor degree in overlap between electrical components and the optic path.

What is claimed is:

1. An intraocular lens ("IOC") adapted to sense intraocular pressure and adapted for implantation in an eye, comprising:
    an optic portion sized and configured to be disposed in a central region of the IOL; and
    a haptic portion that extends radially outward relative to a periphery of the optic portion, the haptic portion comprising a substrate layer extending radially outward relative to the periphery of the optic portion,
    wherein the haptic portion also includes an intraocular pressure sensor secured to the substrate layer,
    the substrate layer also extending radially inward relative to the periphery of the optic portion and through the optic portion,
    wherein the haptic portion further comprises an electronics module disposed on the substrate layer,
    wherein the intraocular pressure sensor is disposed in the electronics module,
    wherein the optic portion comprises an anterior optic portion and a posterior optic portion spaced apart from the anterior optic portion by the substrate layer that extends through the optic portion, the anterior optic portion disposed anterior to the substrate layer in the optic portion, and the posterior optic portion disposed posterior to the substrate layer in the optic portion, and
    wherein the intraocular lens further comprises a folding line along which the IOL is folded for implantation, with a distance between the folding line and the intraocular pressure sensor of about 0.1 mm to about 0.6 mm.

2. The IOL of claim 1, wherein the electronics module further comprises a rechargeable battery and at least one of a microcontroller or an application-specific integrated circuit.

3. The IOL of claim 1, wherein the haptic portion further comprises an antenna secured to the substrate layer.

4. The IOL of claim 1, wherein the anterior optic portion and the posterior optic portion comprise a hydrophobic material.

5. The IOL of claim 1, wherein the anterior optic portion and the posterior optic portion comprise a hydrophilic material.

6. The IOL of claim 1, wherein the anterior optic portion has a first refractive index, and the substrate layer that extends through the optic portion has a second refractive index greater than the first refractive index.

7. The IOL of claim 6, wherein the posterior optic portion has a third refractive index that is the same as the first refractive index.

8. The IOL of claim 6, wherein the first refractive index is from 1.42-1.56 and the second refractive index is from 1.45-1.

9. The IOL of claim 6, wherein an adhesive bonds the anterior optic portion to the substrate layer, wherein the adhesive has a refractive index that is between the first refractive index and the second refractive index.

10. The IOL of claim 9, wherein the adhesive refractive index is a mean of the first refractive index and the second refractive index.

11. The IOL of claim 1, wherein the substrate layer comprises at least one of a polyether, a polyamide, a polyimide, a polyester, or a cyclic olefinic copolymer.

12. The IOL of claim 1, wherein the substrate layer extends radially around the entirety of the periphery of the optic portion.

13. The IOL of claim 1, wherein the substrate layer has a tensile modulus in the range of 2-10 GPa measured at 25° C.

14. The IOL of claim 13, wherein the substrate layer has a melting point in excess of 100° C.

15. The IOL of claim 13, wherein the substrate layer has a glass transition temperature in excess of 75° C.

16. The IOL of claim 1, wherein the substrate layer has a thickness from 5-25 microns and a thickness of the optic portion is from 100-400 microns.

17. The IOL of claim 1, wherein the substrate layer comprises at least two layers, at least one of which comprises a cross-linked thermoset and at least one of which comprises a partially crystalline thermoplastic material.

18. An intraocular lens ("IOL") adapted to sense intraocular pressure and adapted for implantation in an eye, comprising:
    an optic portion sized and configured to be disposed in a central region of the IOL; and
    a haptic portion that extends radially outward relative to a periphery of the optic portion, the haptic portion comprising a substrate layer extending radially outward relative to the periphery of the optic portion,
    wherein the haptic portion also includes an intraocular pressure sensor secured to the substrate layer,
    the substrate layer also extending radially inward relative to the periphery of the optic portion and through the optic portion,
        wherein the substrate layer comprises at least two layers, at least one of which comprises a cross-linked thermoset and at least one of which comprises a partially crystalline thermoplastic material, wherein the haptic portion further comprises an electronics module disposed on the substrate layer,
wherein the intraocular pressure sensor is disposed in the electronics module, and
wherein the optic portion comprises an anterior optic portion and a posterior optic portion spaced apart from the anterior optic portion by the substrate layer that extends through the optic portion, the anterior optic portion disposed anterior to the substrate layer in the optic portion, and the posterior optic portion disposed posterior to the substrate layer in the optic portion.

19. The IOL of claim 18, wherein a first layer of the at least two layers of the substrate layer comprises a cross-linked thermoset and a second layer of the at least two layers of the substrate layer comprises a partially crystalline thermoplastic material.

\* \* \* \* \*